United States Patent
Clauer et al.

(10) Patent No.: US 6,867,390 B2
(45) Date of Patent: Mar. 15, 2005

(54) AUTOMATED POSITIONING OF MOBILE LASER PEENING HEAD

(75) Inventors: Allan H. Clauer, Worthington, OH (US); Jeff L. Dulaney, Dublin, OH (US); David F. Lahrman, Powell, OH (US)

(73) Assignee: LSP Technologies, Inc, Dublin, OH (US)

(*) Notice: Subject to any disclaimer, the term of this patent is extended or adjusted under 35 U.S.C. 154(b) by 0 days.

(21) Appl. No.: 10/372,523

(22) Filed: Feb. 21, 2003

(65) Prior Publication Data

US 2003/0217997 A1 Nov. 27, 2003

Related U.S. Application Data

(63) Continuation-in-part of application No. 09/846,084, filed on Apr. 30, 2001, now Pat. No. 6,528,763.

(51) Int. Cl.[7] ............................................. B23K 26/00
(52) U.S. Cl. ............................... 219/121.85; 219/121.78
(58) Field of Search ..................... 219/121.85, 121.78, 219/121.79, 121.83

(56) References Cited

U.S. PATENT DOCUMENTS 6,288,358 B1 * 9/2001 Dulaney et al. ......... 219/121.6

FOREIGN PATENT DOCUMENTS

GB 2340781 A * 3/2000 ............ C21D/1/09

* cited by examiner

Primary Examiner—M. Alexandra Elve
(74) Attorney, Agent, or Firm—Randall J. Knuth

(57) ABSTRACT

The present invention enables the processing head to locate itself precisely on the surface of the structure being processed, and to then reposition itself correctly for the next laser spot. Further, the present invention will complete processing a laser peened area, the area including a multiplicity of spots arranged in a specific pattern, and correctly laser peen each spot in the area under control of a controller including control linkages with the laser.

The invention further provides an automated laser peening processing head encompassing spatial position sensing and locating means, as well as programmed spatial positioning, application of overlay materials, verification of proper overlay condition and positioning, and notification of the laser to pulse the surface of the structure.

28 Claims, 2 Drawing Sheets

AUTOMATED POSITIONING OF MOBILE LASER PEENING HEAD

This application is a continuation-in-part of U.S. patent application Ser. No. 09/846,084, filed Apr. 30, 2001, now U.S. Pat. No. 6,528,763 entitled, "Laser Search Peening for Exfoliation Corrosion Detection."

BACKGROUND OF THE INVENTION

1. Field of the Invention

The present invention relates to the automated movement of a laser peening head and particularly to the automated positioning of that mobile laser peening head.

2. Description of the Related Art

Current laser peening is typically performed within fixed processing cells. The laser is stationary and the beam delivery system, which transfers the laser beams to a processing cell, is also typically stationary. This results in a fixed laser beam position within the processing cell. A workpiece undergoing laser peening must be moved through the path of the fixed laser beams in a pre-programmed positioning sequence to complete laser peening of the part over the prescribed area on the workpiece.

This program of sequential positions of the workpiece may include a large number of positioning movements to cover the desired laser peened area with a multiplicity of laser peened spots. Each spot represents one position of the workpiece and one laser pulse applied to the workpiece surface. This method has served well for workpieces of relatively small size that can be conveniently moved to a stationary processing cell and manipulated within the cell by a reasonably sized machine tool such as a robot.

However, when extending the use of laser peening to very large structures, such as aircraft wing and fuselage components, it is no longer feasible to construct processing cells and machine tools large enough to process the desired areas on these structures. To laser peen these types of large structures, it is most feasible to use a mobile laser and/or mobile laser beam delivery system to bring the laser beam to the area on the structure to be laser peened, and to reduce the processing cell to a small, mobile processing head that can be easily manipulated over the surface of the area to be laser peened on the surface (see U.S. patent application Ser. Nos. 09/211,553 and 09/846,084, both commonly assigned herewith and fully incorporated by the reference thereto).

The processing head must be able to move over the surface of the area on the structure being processed and to deliver the laser beam and any required overlay materials to the area being processed reproducibly and accurately to accomplish consistent, useful laser peening of the structure. An extremely important step in the processing sequence is to accurately position the laser beam on the surface of the structure. In a stationary workcell wherein smaller workpieces are manipulated in a fixed laser beam path, methods to ensure the proper positioning of the workpiece within the laser beam to accurately laser peen the intended target area are described in an earlier patent application structures (i.e., U.S. patent application Ser. No. 09/564,360, commonly assigned herewith and fully incorporated by reference thereto). That application also addresses manual or operator-controlled positioning of the mobile laser peening head and firing of the laser for each laser pulse for large, stationary. For exfoliation corrosion detection on large structures using a laser peening-related method, a patent filing includes the indexed movement of a robotic laser peening head over a large structure (i.e., U.S. patent application Ser. No. 09/846, 08').

U.S. patent application Ser. No. 09/21,553, concerning a mobile laser peening system, describes a remote processing head, but utilizes operator guidance and alignment of the processing head for each laser pulse through a direct visual system or remote camera viewing system. Automated movement of the head according to a preprogrammed spatial pattern and automated application and/or removal of the overlays is not mentioned.

U.S. patent Application No. 09/846,084, from which this application depends, describes an automated laser search peening head for exfoliation corrosion detection. It specifies automated movement of a robotic processing head over a surface to specific locations and describes indexing the movement of the robot over the surface. However, it does not describe automated location verification methods to be used. The application does not describe automated application and removal of overlays but does describe sequential control of overlay application, laser pulse application, and surface examination for corrosion by a controller.

U.S. Pat. No. 5,790,620, to Okazaki et al, describes a processing head for laser peening underwater in a nuclear reactor shroud and core cooling piping. There is pre-mapping of the interior surfaces by the camera, and subsequent programming of a processing location and pattern into a controller for the processing head. The movement of the processing head or mirror system and lens focusing system within the processing head are automated, being controlled by a controller. Since the operation is carried out under water, there is no automated application of opaque or transparent overlays. The surfaces are processed without an opaque overlay. The programmed motion of the head does not address automated real time location verification and correction to a programmed position on a large structure.

What is needed is an automated method and apparatus to control the movement and positioning of the mobile processing head over the surface of the structure to be laser peened, and in addition to instruct the laser to pulse when the processing head is in upper position and she surface has been made ready for the laser pulse.

SUMMARY OF THE INVENTION

The present invention enables the processing head to locate itself precisely on the surface of the structure being processed, and to then reposition itself correctly for the next laser spot. Further, the present invention will complete processing a laser peened area, the area including a multiplicity of spots arranged in a specific pattern, and correctly laser peen each spot in the area under control of a controller including control linkages with the laser.

The invention further provides an automated laser peening processing head encompassing spatial position sensing and locating means, as well as programmed spatial positioning, application of overlay materials, verification of proper overlay condition and positioning, and notification of the laser to pulse the surface of the structure.

The present invention, in one form thereof, comprises an automated laser peening process apparatus for automated laser peening processing of a workpiece including at least one of a guidance mechanism and an alignment sensor, an application device, a laser beam unit, and a control unit. At least one of the guidance mechanism and the alignment sensor are configured at least for determining an initial processing location within a process area on the workpiece. The application device is for applying at least one process overlay to the process area. The laser beam unit is configured for projecting a laser beam on a chosen process portion of the process area. The laser beam forms a laser spot and generates a pressure pulse and resulting compressive residual stresses on the chosen process portion. A control unit controls each of the at least one of a guidance mechanism and an alignment sensor, the application device, and the laser beam unit. The control unit is operatively linked with each of the at least one of the guidance mechanism and the alignment sensor, the application device, and the laser beam unit.

The present invention, in another form thereof, comprises a method of automatically laser peening a workpiece that includes a series of steps. A mobile process head as provided, the process head carrying a plurality of process head elements. The process head elements include at least one alignment sensor, an application device configured for applying at least one process overlay, and a laser beam unit configured for generating a processing beam. A process control unit is provided and configured for controlling the process head and each alignment sensor, the application device, and the laser beam unit carried by the process head. The process head is placed in a general location of a processing pattern on the workpiece. An initializing locating procedure using the control unit and at least one the alignment sensor is performed to determine an initial position of the process head on the workpiece relative to the processing pattern. The process head is positioned so as to correspond to a starting position of the processing pattern as opposed to the initial position. A laser peening process is initiated at the starting position.

An advantage of the present invention is that the system allows the workpiece to remain stationary during processing while permitting laser processing of a potentially large area of that workpiece.

Another advantage of the present invention is that the system provides a combined sensor and control system that facilitates immediate verification of the proper performance of step (e.g., process head movement, overlay application, laser firing) and permits immediate compensation and/or correction for a step not properly executed initially.

Yet another advantage of the present invention is that the mobile processing unit is configured to carry the overlay application unit(s), laser unit, sensory equipment, and any other related processing/treatment units together, making the mobile processing unit alone able to facilitate start-to-finish laser peening processing of a given location (one to three dimensions) of a given workpiece.

An even further advantage of the present invention is that it is potentially applicable to the treatment of a variety of components including, e.g., aircraft structures (frames, bulkheads, wings, landing gear, fuselages, etc.), large turbine rotors and bearing housings, nuclear waste storage casks, nuclear power systems, large ship components, large power generation components (e.g., land-based turbines, windmill power generation systems, etc.), large cranes and construction equipment, building structures (e.g., girders, beams, and metal bridges).

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
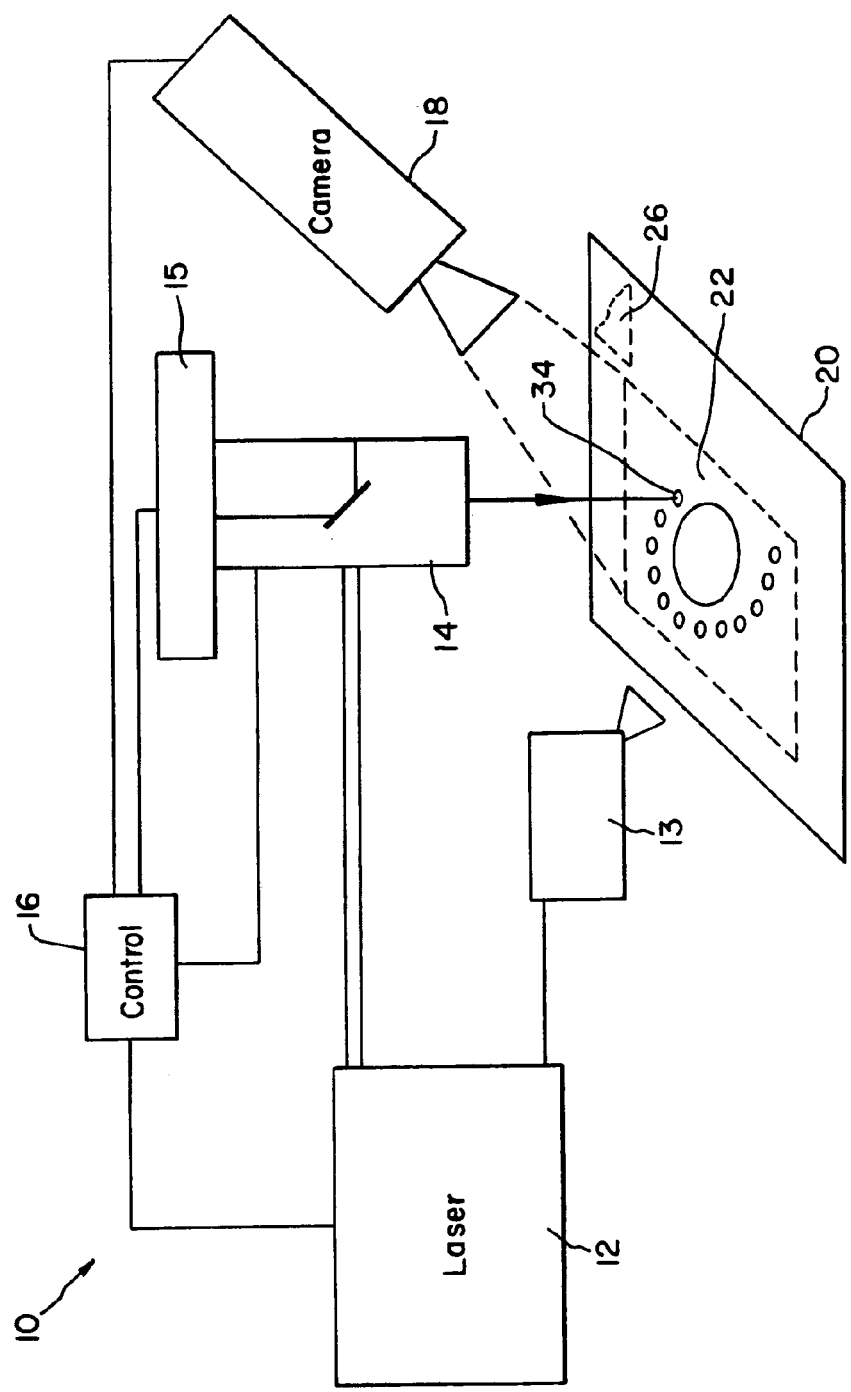
FIG. 1 is a schematic view of the laser processing system of the present invention.
Figure 2:
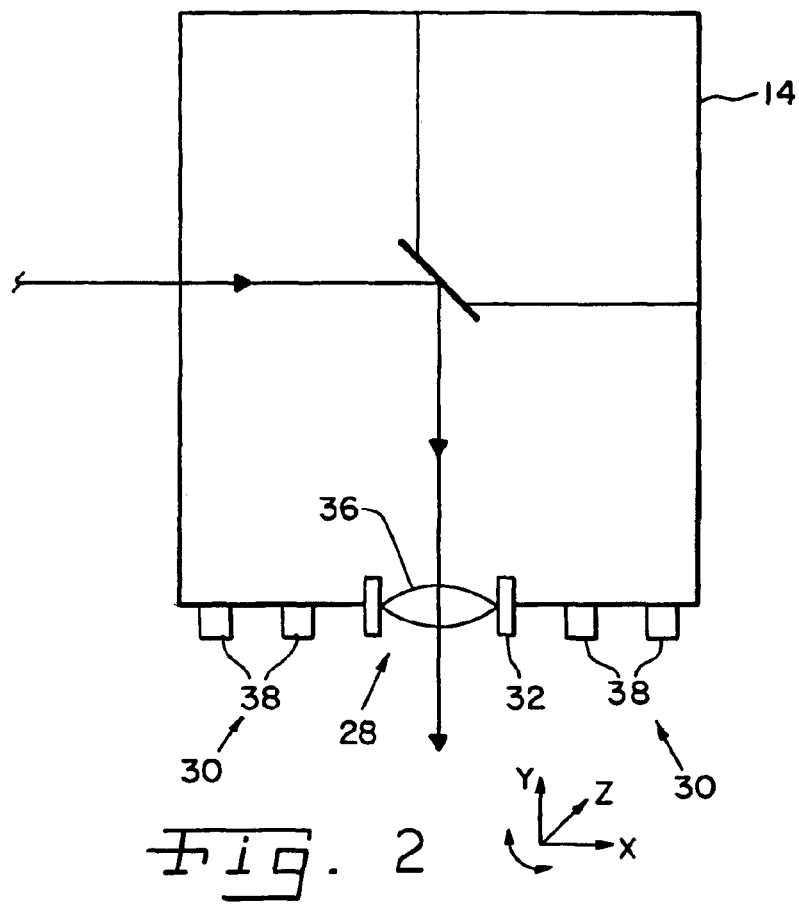
FIG. 2 is a is a schematic view of the process head shown in FIG. 1.
Figure 3:
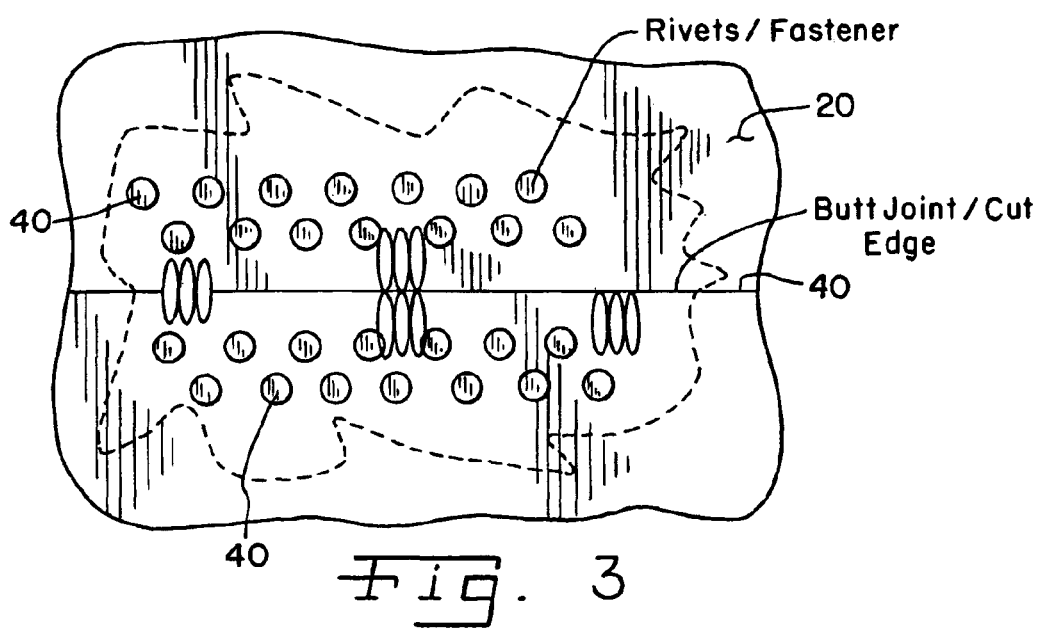
FIG. 3 is an embodiment of a structure to be treated by she laser processing system of FIG. 1.

Referring now to the drawings and particularly to FIG. 1, there is shown the laser peening/processing system 10 of the present invention having a laser instrument 12, a laser search peen/process head 14 connected to the laser instrument, and a controller means 16 connected to control the laser instrument 12, laser search peen head 14, overlay applicator mechanism 13, positioning mechanism 15 and inspection instrument 18.

Detection system 10 directs laser search peen head 14 to laser search peen area 22, and during this process, overlay applicator mechanism 13 applies the processing overlay or overlays as sequenced from controller 16, and laser system 12 then delivers a laser pulse to laser search peen head 14. As shown, system 10 is capable of detecting exfoliation corrosion, via camera 18 on significant portions of structure 20 (e.g., aluminum alloy plate section) as well as other surfaces, by examining the laser search peened surface 22 from low magnification to high magnification depending primarily on the optics and resolution of camera 18. This magnification could be in the range of, for example, 0 to 30×but is not limited to this range. Other detection means, such as direct visual examination of plate 20 or other ways, may also be utilized to perceive and/or confirm exfoliation delamination within the laser spot areas 22.

Upon completion of the inspection of area 22 with camera 18 for evidence of exfoliation determination within area 22, the laser system 10, or portion thereof, can be indexed to the next area 26 to be laser search peened. The positioning mechanism 15 is operatively linked with controller 16 and is configured for indexing the detection system 10 or laser search peen/process head 14 from one location 22 to the next location 26.

The laser search peen/process head 14 of the present invention includes both a locating means 28 and a position sensing means 30.

The locating means 28, in the embodiment shown, includes a robotic module 32 that is able to move over the surface of a structure 20 such as an aircraft wing, wing spar, bulkhead or fuselage skin as described in U.S. patent application Ser. No. 09/846,084, the parent application hereof. This locating mechanism 28 has the ability to adjust the laser beam spot 34 to maintain the desired spot position, area, size, and/or and nominal shape. In a lens-based beam delivery system, the robotic system 32 is configured to enable the lens 36 to be moved in an XYZ coordinate space and rotationally around appropriate rotational axes lying within the plane of lens 36. The XYZ coordinate space is referenced to the nominal orientation of the plane of the target area to be processed for each pulse.

The spatial position sensing means 30 includes at least one alignment/position sensor 38 suitable to the structural geometry and processing requirements of the structure 20 being laser peened. The sensing means 30 advantageously includes several and/or various types of sensors 38, such as, e.g., laser positioning sensors, video imaging sensors, photo sensors, and echo-location sensors, all to accomplish verification of the immediate location and orientation of the processing head 14 on the structure 20. Laser positioning sensors use significant features 40 of the structure 20, such as surfaces of fasteners, lugs, stiffeners, holes, edges and the surface being processed to triangulate the position and orientation of the processing head 14 on the structure 20. The position sensing means 30 can instead/also use predetermined data points, which may be provided by the manufacturer.

Video imaging sensors use the appearance, size and relative location of outstanding features 40 of the structure 20 compared to computer-stored images to determine the position and orientation of the processing head 14. Photo (electromagnetic radiation, non-laser) sensors also use the position of reflected light (electromagnetic radiation) beams from mirrors (not shown) appropriately attached to the structure 20 for position and orientation determination. The light (electromagnetic radiation) beam sources would be affixed to the processing head 14 and directed toward selected mirrors. The combination of the positions of the reflected beams on photo (electromagnetic radiation) sensor arrays, also fixed to the processing head 14, would enable determination of the location and orientation of the processing head 14.

Alternately, an echo-location technique could be employed. Echo-location uses highly directional sound pulses directed towards reflectors affixed to the structure 20 being processed, similar to the mirrors of the light-based system. The sound pulses would originate from emitters (not shown) fixed to the processing head 14 and would be picked up by highly directional sensors, also fixed to the processing head 14.

Prior to beginning processing of the structure surface, controlling device 16 is programmed with the laser peening spot position pattern to be performed on the surface of the structure 20. The program is structured with reference to the spatial coordinates of the locating features set up for the particular spatial sensing system 30 being used. Upon initially placing the processing head 14 into the general location of the processing pattern on the structure surface and orienting the individual sensors 38 to the appropriate surface reference feature 40 according to established calibration and setup procedures, the processing head performs an initializing locating procedure to determine its initial position on the structure 20 with regard to the processing pattern. After initializing its position, it moves to the starting position for the laser peening process and begins the laser peening sequence.

Through links between the processing head 14 and the process controller 16, the processing head 14 communicates that it is in position to begin laser peening, and the controller 16 issues a sequence of processing commands. Such commands are followed individually by actions and notifications of completion of such actions by the processing head 14 to thereby complete the processing of the area automatically. A typical sequence of tasks would be: move to the next position; verify that the processing head 14 as in position; use applicator mechanism 13 to apply the opaque overlay; verify the overlay is in place and correctly applied; use applicator mechanism 13 to apply the transparent overlay; verify the overlay is in place and correctly applied; fire the laser; verify that the laser has fired with a monitored effect on the target (e.g., plasma monitoring and perhaps monitoring that the laser spot was the correct size and in the correct position); conduct any post-processing tasks on the spot; and verify completion of any such post-processing task (e.g., water wash, etc.).

This fully-automated sequence represents the use of all of the elements of an automated process sequence. However, it is not necessary to include all such elements to be within the scope of the present invention. Advantageously, at least the positioning of the laser processing/peening head and the firing of the laser system are both automated.

It is understood that laser peening/processing head 14 can be used for peening, as primarily disclosed, or for performing other laser shock processing steps (e.g., structural testing).

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which tall within the limits of the appended claims.

What is claimed is:

1. An automated laser peening process apparatus for automated laser peening processing of a workpiece, comprising:

a laser beam unit configured for projecting a laser beam on a chosen process portion of a process area of the workpiece, the laser beam forming a laser spot and generating a pressure pulse and resulting compressive residual stresses on the chosen process portion;

at least one of a beam locating mechanism and a position sensing device, said beam locating mechanism being configured for adjusting at least one characteristic of the laser spot, said position sensing device being configured to automatedly determine a spatial relationship of at least one feature of said apparatus relative to at least one of said workpiece and a laser peening processing pattern for said workpiece, the spatial relationship defining a relative position indicative of at least one of location and orientation;

an application device for applying at least one process overlay to the process area; and a control unit for controlling operation of said laser beam unit, said at least one of said beam locating mechanism and said position sensing device, and said application device, said control unit being operatively linked with said laser beam unit, said at least one of said beam locating mechanism and said position sensing device, and said application device.

2. The automated laser peening process apparatus of claim 1; wherein said laser beam unit, said at least one of a locating mechanism and said position sensing device, and said application device are conjunctively movable relative to one another.

3. The automated laser peening process apparatus of claim 1, wherein said position sensing device is further configured for automatically verifying an actual location and an actual orientation of at least said laser beam unit.

4. The automated laser peening process apparatus of claim 3, wherein the control unit is configured for initiating a correction in at least one of the actual location and the actual orientation of at least the laser beam unit when the at least one of the actual location and the actual orientation is not within an acceptable range limit of a programmed position and orientation.

5. The automated laser peening process apparatus of claim 3, wherein said position sensing device including at least one of a laser positioning sensor, a video imaging sensor, a photo sensor, and an echo-location sensor.

6. The automated laser peening process apparatus of claim 3, wherein said position sensing device including at least one alignment/position sensor, at least one said alignment/position sensor being configured for detecting a presence and proper alignment of at least one of said process overlay.

7. The automated laser peening process apparatus of claim 6, wherein said at least one said alignment/position sensor is configured for instructing said control unit to permit activation of the laser beam unit upon the detection of the presence and proper alignment of at least one said process overlay.

8. The automated laser peening process apparatus of claim 1, wherein each said process overlay is one of a transparent and opaque overlay.

9. The automated laser peening process apparatus of claim 1, wherein at least one said characteristic of the laser spot being one of an associated spot position, spot area, spot size, and nominal spot shape.

10. The automated laser peening process apparatus of claim 9, wherein said beam locating mechanism includes an adjustable lens-based beam delivery system, the adjustable lens-based beam delivery system having a lens configured for at least one of linear and rotational movement relative to an XYZ axis set.

11. The automated laser peening process apparatus of claim 1, further including a mobile processing head, the mobile processing head carrying said at least one of said beam locating mechanism and said position sensing device, the application device, and the laser beam unit, said mobile processing head being operatively linked with the control unit.

12. The automated laser peening process apparatus of claim 11, wherein said mobile processing head is configured for robotic movement via said control unit.

13. A method of automatically laser peening a workpiece, comprising the steps of:
providing a mobile process head, said process head carrying a plurality of process head elements, said process head elements including a position sensing device, an application device configured for applying at least one process overlay, and a laser beam unit configured for generating a processing beam;
providing a process control unit configured for controlling said process head and said position sensing device, said application device, and said laser beam unit carried by said process head;
placing said process head in a general location of a processing pattern on the workpiece;
performing an initial locating procedure using said control unit and said position sensing device to determine an initial position of said process head on the workpiece relative to the processing pattern;
positioning said process head so as to correspond to a starting position of the processing pattern; and
initiating a laser peening process at the starting position.

14. The method of claim 13, wherein the workpiece has at least one appropriate surface reference feature associated therewith, the step of performing an initial locating procedure includes the substeps of orienting said position sensing device to at least one said appropriate surface reference feature, sensing at least one of a feature position and a feature orientation of said at least one said appropriate surface reference feature, and using at least one of a triangulation technique and a calibration and set-up procedure to determine the initial position of said process head based upon the at least one of a feature position and a feature orientation of each said appropriate surface reference feature.

15. The method of claim 13, wherein the step of initiating a laser peening process further includes the sub-steps of:
issuing a sequence of process commands from said control unit to said process head and said plurality of process head elements carried thereby; and
performing a sequence of process actions with at least one of said process head and said plurality of process head elements, the sequence of process actions being based upon the sequence of process commands.

16. The method of claim 15, further including the sub-step of notifying said control unit of a proper completion of a given process action so as to thereby indicate that a next process action in the sequence of process actions can then be performed.

17. The method of claim 13, wherein the step of initiating a laser peening process further includes the sub-steps of:
verifying a proper positioning of said processing head, thereby establishing a verified head position;
applying an opaque overlay material on the workpiece at the verified head position;
verifying a proper positioning and application of the opaque overlay, thereby establishing a verified coating of opaque overlay material;
applying a transparent overlay material on the verified coating of opaque overlay material;
verifying a proper positioning and application of the transparent overlay, thereby establishing a verified coating of transparent overlay material; and
firing a laser beam at the verified head position upon verifying a proper positioning and application of the opaque overlay and the transparent overlay.

18. The method of claim 17, further including the sub-step of verifying that the laser beam has fired with an appropriate monitored effect.

19. The method of claim 18, wherein an appropriate monitored effect includes at least one of appropriate plasma generation, beam spot size, and beam spot position.

20. The method of claim 17, further including the sub-steps of conducting at least one post-processing task and verifying a completion thereof.

21. The method of claim 17, further including the steps of:
moving said process head to a next process location of the processing pattern;
verifying a proper positioning of said processing head at the next process location, thereby establishing a next verified head position;
applying an opaque overlay material on the workpiece at the next verified head position;
verifying a proper positioning and application of the opaque overlay, thereby establishing a verified coating of opaque overlay material;
applying a transparent overlay material on the verified coating of opaque overlay material;
verifying a proper positioning and application of the transparent overlay, thereby establishing a verified coating of transparent overlay material; and
firing a laser beam at the next verified head position upon verifying a proper positioning and application of the opaque overlay and the transparent overlay.

22. The method of claim 21, further including the step of verifying that the laser beam has fired with an appropriate monitored effect.

23. The method of claim 21, further including the steps of conducting at least one post-processing task and verifying a completion of at least one the post-processing task.

24. The automated laser peening process apparatus of claim 1, wherein said control unit being configured to automatically control operation of said laser beam unit, said at least one of said beam locating mechanism and said position sensing device, and said application device.

25. The automated laser peening process apparatus of claim 1, wherein said control unit being configured to coordinate operation of said laser beam unit, said at least one of said locating mechanism and said position sensing device, and said application device according to an automatic control process, the automatic control process being configured to facilitate positioning of said apparatus to a current processing position, application of the at least one process overlay, operation of said laser beam unit, and repositioning of said apparatus to a next processing position.

26. The automated laser peening process apparatus of claim 1, further includes a first device configured to selectably move at least one component of said apparatus, said control unit being configured to control operation of said first device.

27. The automated laser peening process apparatus of claim 1, wherein the determination of spatial relationship by said position sensing device includes an initial position determination.

28. The automated laser peening process apparatus of claim 1, wherein the at least one apparatus feature pertaining to the spatial relationship determination by said position sensing device includes an indication of laser beam propagation path.

* * * * *